United States Patent [19]

Maldonado et al.

[11] Patent Number: 4,563,477

[45] Date of Patent: Jan. 7, 1986

[54] PROCESS FOR THE PREPARATION OF ALPHA-(N-PYRROLYL)-DERIVATIVE ACIDS, THE SALTS AND ESTERS THEREOF; ALPHA-(N-PYRROLYL)-PHENYLACETIC ACIDS, THE ESTERS THEREOF, PHARMACEUTICAL COMPOSITIONS CONTAINING THEM AND THERAPEUTICAL APPLICATIONS THEREOF

[75] Inventors: Francisco S. Maldonado; Luis C. Plá; José L. F. Puentes, all of León; José M. F. Sousa-Faro, Villanueva de la Canada, all of Spain

[73] Assignee: Antibioticos, S.A., Spain

[21] Appl. No.: 494,382

[22] Filed: May 13, 1983

[30] Foreign Application Priority Data

May 17, 1982 [ES] Spain .................... 512.268

[51] Int. Cl.$^4$ .................. A61K 31/40; C07D 207/327
[52] U.S. Cl. ........................ 514/427; 548/562
[58] Field of Search ................ 546/562; 514/427

[56] References Cited

FOREIGN PATENT DOCUMENTS 492589 6/1981 Spain .

OTHER PUBLICATIONS

Almmany Juarez I, Chem. Abs. 96, 217578 (Jun. 1, 1981).

Almmany Juarez II, Chem. Abs. 95, 42977r (1979).

*Primary Examiner*—Mark L. Berch
*Attorney, Agent, or Firm*—McGlew and Tuttle

[57] ABSTRACT

A process for the preparation of alpha-(N-pyrrolyl)-derivative acids, the salts and esters thereof, of the formula

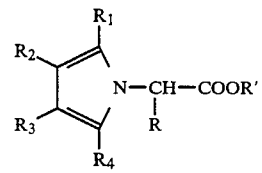

in which R, $R_1$, $R_2$, $R_3$ and $R_4$ are hydrogen atoms or substituted or unsubstituted alkyl, aryl, alkylaryl or heterocyclic radicals and R' is a metal cation, an organic base or an organic radical, wherein the corresponding amino ester is reacted with a dialkoxytetrahydrofuran or a derivative thereof. Certain compounds comprised among those corresponding to the above formula, particularly the DL, D and L-alpha-(N-pyrrolyl)-phenylacetic acids and certain esters thereof. Therapeutical compositions containing such compounds as active ingredient and therapeutical applications of said compounds.

13 Claims, 3 Drawing Figures

PROCESS FOR THE PREPARATION OF ALPHA-(N-PYRROLYL)-DERIVATIVE ACIDS, THE SALTS AND ESTERS THEREOF; ALPHA-(N-PYRROLYL)-PHENYLACETIC ACIDS, THE ESTERS THEREOF, PHARMACEUTICAL COMPOSITIONS CONTAINING THEM AND THERAPEUTICAL APPLICATIONS THEREOF

FIELD OF THE INVENTION

This invention relates to a process for the preparation of alpha-(N-pyrrolyl) derivative acids, the salts and esters thereof, of Formula I:

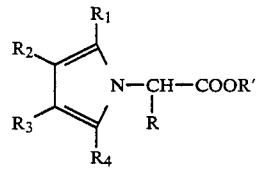

(I)

in which R, $R_1$, $R_2$, $R_3$ and $R_4$ are hydrogen atoms or substituted or unsubstituted alkyl, aryl, alkylaryl or heterocyclic radicals.

R' is a metal cation, an organic base or an organic radical.

The invention relates also to certain compounds comprised among those having the Formula I, particularly to:

Ethyl DL($\pm$)-alpha-(N-pyrrolyl)-phenylacetate
Dibenzylammonium DL($\pm$)-alpha-(N-pyrrolyl)-p-hydroxy-phenylacetate
DL($\pm$)-alpha-(N-pyrrolyl)-phenylacetic acid
D(+)-alpha-(N-pyrrolyl)-phenylacetic acid
L(−)-alpha-(N-pyrrolyl)-phenylacetic acid The invention also relates to compositions comprising the above mentioned compounds which have therapeutic application for their platelet antiaggregation activity or for their analgesic activity.

STATE OF THE ART

The compounds of the general formula I may be prepared by converting the amino group of an amino acid or ester thereof of general formula

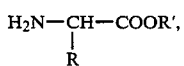

in which R and R' are as above defined in the N-substituted pyrrole, by reaction with furan or a derivative thereof.

Clauson-Kaas and Tyle [Acta·Chem. Scand. 6, 667 (1952)] described the methoxylation of 2(acetamidomethyl)-furan (Formula II) to 2,5-dimethoxy-2(acetamidomethyl)-2,5-dihydrofuran (Formula III). This compound was hydrogenated with catalyst to give 2,5-dimethoxy-2(acetamidomethyl)-tetrahydrofuran (Formula IV), which with aniline in acetic acid medium gave 1-phenyl-2-(acetamidomethyl)-pyrrole (Formula V), with a mean yield of 81% according to the following scheme:

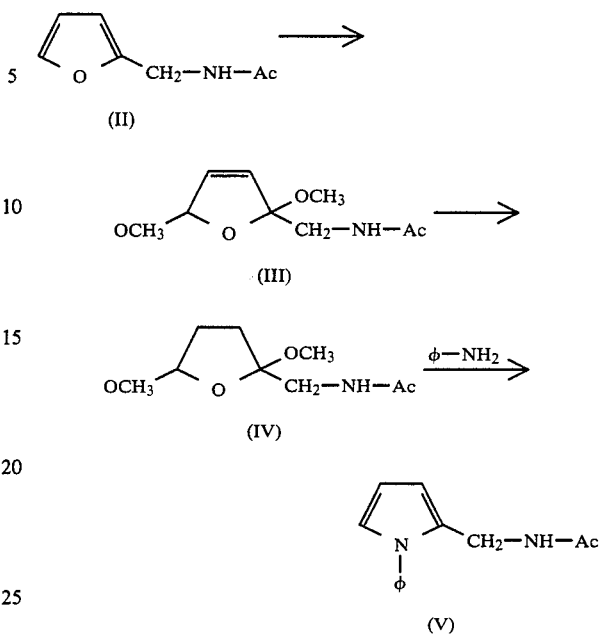

Subsequently Clauson-Kaas and Tyle described a general method for the preparation of N-substituted pyrroles by reaction of 2,5-dialkoxytetrahydrofuran with primary amines.

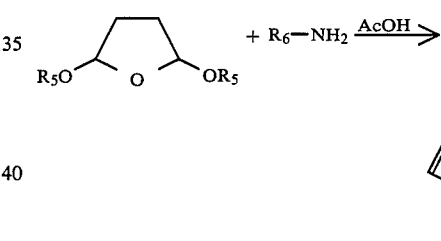

in which $R_5$ stands for methyl or ethyl radicals and $R_6$ stands for alkyl or aryl radicals. Kaas et al applied the foregoing reaction to various aromatic and aliphatic amines.

SUMMARY OF THE INVENTION

The compounds to which the present invention relates may be prepared from the alpha amino acids or esters thereof, by reaction with 2,5-dialkoxytetrahydrofuran in acetic acid medium at boiling temperature. The most used alkoxytetrahydrofurans are 2,5-dimethoxy and 2,5-diethoxy. Higher conversion yields are usually obtained with the former. When a large excess of sodium acetate dissolved in the glacial acetic acid is used in the reaction medium, the reaction time may be drastically reduced. The said reactions may be schematically expressed as follows:

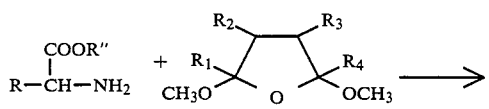

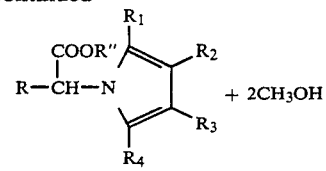

in which R, $R_1$, $R_2$, $R_3$ and $R_4$ are as hereinbefore defined and R" also has the same meaning thereas.

As stated hereinbefore, the corresponding amino acids may be used as starting products, but higher yields are obtained when the esters thereof are used as starting products. Although any of the esters (benzyl, nitrobenzyl, methyl, etc.) could, in principle, be used, the most frequently used are the methyl and ethyl esters.

To prepare the methyl, ethyl, etc., esters of the amino acids, there is taken a suspension of the amino acid in the appropriate absolute alcohol and a current of dry HCl gas is blown thereover. After dissolution, which takes place with release of a substantial amount of heat, the solution is chilled in an ice bath and the supply of dry HCl gas is continued to saturation. The solution is thereafter left for 3-4 hours at room temperature, protected from moisture. It is finally concentrated to dryness, is dissolved in the corresponding alcohol and crystallised by the addition of ether.

The esters of alpha-amino acids (both in free form and as hydrochlorides) are reacted in glacial acetic acid or in acetic acid/sodium acetate medium at boiling temperature for times varying between one minute and about one hour. After the reaction time has elapsed, the mixture is cooled and the N-pyrrolyl derivative is removed by fractional distillation under vacuum or with liquid-liquid extraction.

In the latter case, although other solvents may be used, good results are obtained by dissolving the reaction mixture with water and extracting the N-pyrrolyl derivative ester with ethyl acetate. The solvent is subsequently driven off to give the N-pyrrolyl derivative ester with an acceptable purity.

The N-pyrrolyl derivative ester may be hydrolysed with any of the known processes. Good yields are obtained when the ester is dissolved in a mixture of dioxane-water and a slight excess of an alkaline hydroxide is added. At room temperature, the hydrolysis proceeds readily in times between 15 minutes and several hours. Just as dioxane-water is used, any other mixture of solvents may be used.

Once the organic solvent has been driven off by evaporation under vacuum, the aqueous alkaline solution of the alpha-(N-pyrrolyl) derivative acid is extracted with an organic solvent (ethyl acetate, methylene chloride, chloroform, MIBK, etc) at acid pH, from which it is crystallised by concentration and/or addition of an insolubilising solvent, such as petroleum ether, n-hexane, etc.

As stated hereinbefore, it is also possible to start from the free amino acid. In this case, the amino acid is solubilised in dimethylformamide by addition of p-toluene sulphonic acid, followed thereafter by the addition of the stoichiometric amount of the dialkoxytetrahydrofuran, with heating under reflux for a time of 20 to 60 minutes. After the reaction has terminated, the mixture is cooled and diluted with water, extracted with sulphuric ether and the DMF-water phase, after removal of all the sulphuric ether, is allowed to crystallise in a refrigerator and the corresponding N-pyrrolyl derivative acid is obtained.

N-substituted pyrroles may also be prepared using the metallo-pyrroles as intermediates. The most frequently used are the pyrrolyl magnesium derivatives, formed by reaction of the pyrrole with Grignard reagents.

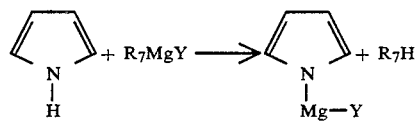

in which Y is a hydrogen atom and $R_7$ has the same meaning as R, except hydrogen.

It is also possible to start from alpha-halogen acid derivatives, reacting them with pyrrole or one of the derivatives thereof.

BRIEF DESCRIPTION OF THE DRAWINGS

Reference is made in the Examples appearing hereinafter to FIGS. 1 to 3.

In all of them the % transmittance is given on ordinates and the wave number ($cm^{-1}$) and wavelength in microns are given on abscissae.

EXAMPLE 1

Ethyl alpha-phenylglycinate hydrochloride

A current of dry HCl was blown over a suspension of 50 g of alpha-phenylglycine in 500 ml absolute ethanol. The amino acid was dissolved with substantial heat development.

After the amino acid had dissolved, the reaction mixture was cooled in an ice bath, the blowing of the dry HCl continuing to saturation, at a temperature of 0°-5° C. Thereafter the flow of HCl was discontinued and the reaction mixture, duly protected from moisture, was left to stand for 3-4 hours at room temperature. Thereafter the reaction mixture was concentrated under vacuum, at a temperature below 50° C. until dry. The residue was dissolved in 200 ml of absolute ethanol and the concentration to dryness was repeated.

The residue was dissolved in 150 ml of absolute ethanol and was crystallised by the addition of 600 ml of ethyl ether. The mixture was left in the refrigerator until the following day. It was finally filtered, washed with 50 ml of sulphuric ether. Weight of product obtained: 62.8 g (88%).

EXAMPLE 2

Figure 1:
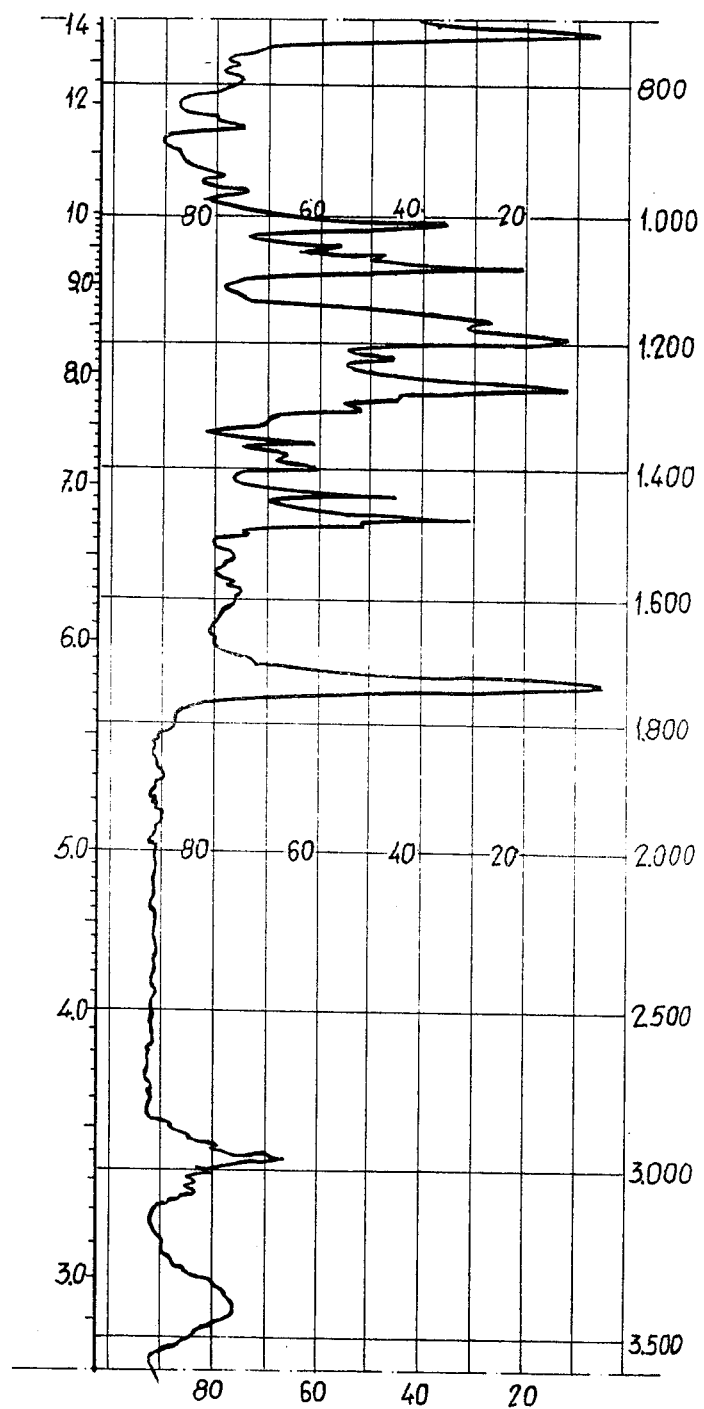
FIG. 1 is the IR spectrum in 0.5% KBr of ethyl alpha-(N-pyrrolyl)-phenylacetate.

Ethyl alpha-(N-pyrrolyl)-phenylacetate 52.8 g (0.24 mole) of ethyl phenylglycinate were dissolved in 136 mil of glacial acetic acid. Thereafter 39 g (0.24 mole) of 2,5-diethoxytetrahydrofuran were added over 10-15 minutes with stirring. The mixture was heated under reflux for one hour. After this time had elapsed, the mixture was allowed to cool and the major portion of the acetic acid was drawn off under reduced pressure. Finally, the residue was distilled under vacuum and the fraction distilling out at 115°-118° C. at 0.2 mm Hg was collected. The product obtained was first a colourless oil which crystallised on cooling, adopting a waxy aspect and weighing 46.5 g (70%). M.p. 51°-53° C. Centesimal composition: 73.31% C.; 6.08% N; 6.53% H. The IR spectrum in 0.5% KBr is illustrated in FIG. 1.

EXAMPLE 3

Alpha-(N-pyrrolyl)-phenylacetic acid 18.5 g of KOH (0.33 mole) were dissolved under heating in a mixture of 65 ml of ethylene glycol and 13 ml of water. 52.2 g (0.23 mole) of ethyl alpha-(N-pyrrolyl)-phenylacetate were added over the above solution with stirring, with heating under reflux (112°-120° C.) for 5 hours.

When the above time had elapsed, the reaction mixture was cooled and poured over a solution formed by 100 ml of water and 100 ml of 96% ethanol. The mixture was acidulated with 2N HCl to pH 2. After one hour under stirring with cooling (5° C.), the mixture was filtered and dried. The dry product weighed 36 g, representing an 80% yield.

Figure 2:
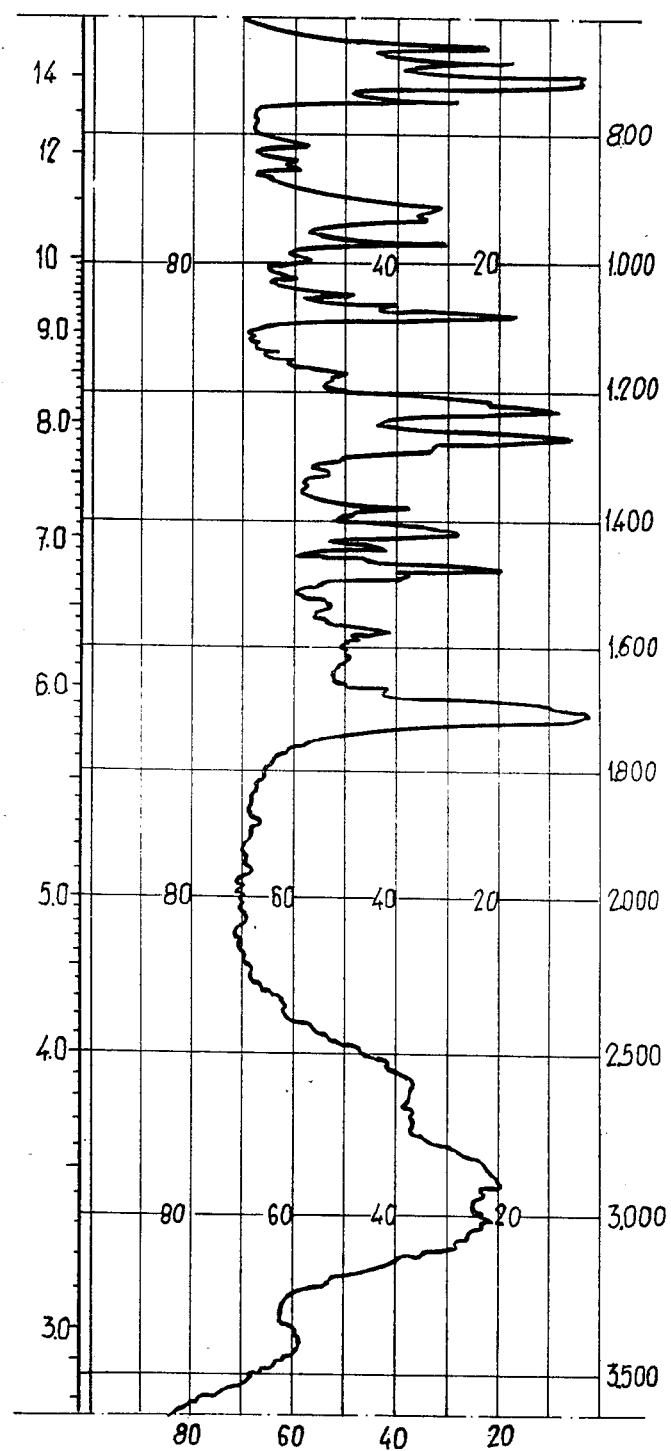
FIG. 2 is the same for alpha-(N-pyrrolyl)-phenylacetic acid.

The product obtained was dissolved in 100 ml of chloroform, was treated with activated carbon and filtered. The filtrate was concentrated under vacuum to ⅓ of the initial volume, followed by the addition of 70 ml of methylcyclohexane. The product obtained, after drying, weighed 27 g (75%), m.p. 127° C. Neutralization equivalent 204. Centesimal composition 71.6% C; 5.52% H; 6.90% N. (Theoretical: 71.64% C.; 5.47% H; 6.97% N). Shows no optical activity. The IR spectrum in 0.5% KBr is given in FIG. 2. 730 cm$^{-1}$ (asymmetrical deformation of the ring CH); 1090 cm$^{-1}$ (symmetrical deformation of the ring CH).

EXAMPLE 4

Alpha-(N-pyrrolyl)-phenylacetic acid 21.6 g (0.1 mole) of ethyl phenylglycinate hydrochloride were added over a solution of 50 g of sodium acetate in 500 ml of glacial acetic acid, heated to reflux. After dissolution, 16.5 ml (0.1 mole) of 2,5-dimethoxytetrahydrofuran were added.

The reaction mixture was heated for one minute. At the end of this time, the reaction mixture was poured over about 1000 g of ice. The aqueous solution was extracted twice with ethyl acetate, the first time with 550 ml and the second time with 250 ml. The organic phases were mixed together and washed with 350 ml of 5% Na$_2$CO$_3$ aqueous solution and thereafter with 350 ml of a saturated sodium chloride solution (twice). The organic phase was evaporated in rotovapor to dryness at a temperature below 50° C. The residue was dissolved in 250 ml of 50% dioxane-water and a sufficient amount of 2N NaOH was added to a constant high alkalinity. Stirring was continued for 1 hour and the mixture was then allowed to stand until the following day.

The pH was then 13 and was lowered to pH 6.5 with 5N HCl. The mixture was concentrated in the rotovapor to remove the dioxane. The volume was topped up to 250 ml with water. The mixture was extracted twice with 200 ml of chloroform at pH 1.5-2 each time. The chloroform phases were mixed together were concentrated in the rotovapor to approximately 100 ml and were crystallised by the addition of petroleum ether. The product obtained weighed 12.9 g (yield=64%) after being dried.

EXAMPLE 5

Alpha-(N-pyrrolyl)-phenylacetic acid 15.1 g (0.1 mole) of alpha-phenylglycine were resuspended in 450 ml of dimethylformamide, followed by the addition of 15 g of p-toluene sulphonic acid and 13.2 g (0.1 mole) of 2,5-dimethoxytetrahydrofuran. The mixture was heated to boiling, and at about 95° C. all the solid product was dissolved, the boiling temperature being held for about 60 minutes. After this time, the mixture was cooled, 400 ml of cold water were added and the total mixture was cooled to between 0°-5° C. The mixture was extracted twice with 200 ml of ethyl ether each time, the ether phases being discarded. The aqueous phase was extracted with 500 ml chloroform at pH 1.5. The chloroform extract was treated with 600 ml water and the pH was adjusted to 11. After separating the phases, 500 ml of chloroform were added to the aqueous extract, the pH being adjusted to 1.5 with 2N HCl. The chloroform phase was concentrated to obtain an oil which was crystallised from methanol-water. After drying, the alpha-(N-pyrrolyl)-phenylacetic acid obtained weighed 5.8 g.

EXAMPLE 6

Dibenzylammonium DL(±)alpha-(N-pyrrolyl)-p-hydroxy-phenylacetate 50 g of sodium acetate were dissolved in 500 cc of acetic acid. 23.2 g (0.1 mole) of ethyl p-hydroxy-phenylglycinate were added over the solution. The resulting solution was heated to boiling and thereafter 15.3 g (0.11 mole) of dimethoxytetrahydrofuran were added, boiling being maintained for one minute.

After this time the reaction mixture was added over 1.5 kg of an ice-water mixture, followed by extraction twice with ethyl acetate.

The ethyl acetate extracts were reunited together and washed with 5% Na$_2$CO$_3$ first and then with a saturated NaCl solution. Finally, the ethyl acetate extract was concentrated under vacuum to remove the major portion of the solvent, 150 ml of dioxane and 100 ml of 2N NaOH were added and stirring was maintained for 2 hours at room temperature.

The reaction mixture was allowed to stand overnight, also at room temperature.

190 ml of water were added and the mixture was neutralised to pH 7.5 with 6N HCl, thereafter the dioxane was removed from the mixuture by vacuum distillation.

180 ml of chloroform were added and the pH was adjusted to 2 with 6N HCl, the phases being separated thereafter. The aqueous phase was extracted again with 60 ml chloroform. The chloroform extracts were reunited and the aqueous phase was discarded.

200 ml of water were added to the chloroform extract, the pH was adjusted to 7.5 with 5N NaOH, the phases being separated thereafter.

The chloroform phase was extracted again with 100 ml water. The aqueous extracts were reunited and diluted to about 600 ml. 180 ml of a 15% aqueous solution of dibenzylammonium acetate (DBA) were added slowly over the previous solution. The addition was held under stirring and cooling for 1½ hours, after which it was filtered and washed with cold water.

The product was dried at 40° C. under vacuum to give a weight of 7.3 g of the dibenzylammonium salt of alpha-(N-pyrrolyl)-p-hydroxy-phenylacetic acid, m.p. 175°-179° C. The IR spectrum in 0.5% KBr showed the typical bands of the N-pyrrol derivatives (1080 cm$^{-1}$, symmetrical deformation of the ring CH and 730 cm$^{-1}$, asymmetrical deformation).

EXAMPLE 7

Separation of alpha-(N-pyrrolyl)-phenylacetic acid enantiomers 35.1 g of yohimbine hydrochloride were dissolved in 1,800 ml of warm water at 40°/50° C. After dissolving, the base yohimbine was precipitated out by the addition of 2N ammonia up to constant pH 9. After 2 hours in a refrigerator (4° C.), it was filtered and washed with water, the cake being allowed to drain well. Without being dried, the whole of the precipitated base yohimbine was poured over a mixture formed by 1,381 ml of water and 284 ml of ethanol containing 18 g of alpha-(N-pyrrolyl)-phenylacetic acid dissolved therein.

The suspension was refluxed for 1 hour, after which it was filtered while warm, an insoluble solid being separated which, after drying, weighed 17 g. The filtrate was allowed to cool, needles appearing after a short time which grouped together in rose form. Once cooled to room temperature, the solid was left in the refrigerator at 4° C. The following day it was filtered and washed with water and dried at 4° C. under vacuum. The dry product weighed 26 g.

The mother liquors were concentrated under vacuum to the onset of crystallisation (approximately half of the initial volume). Thereafter the pH was adjusted to 9 with 2N ammonium hydroxide and the base yohimbine was allowed to crystallise for 1 hour. Thereafter it was filtered and washed with water and finally the base yohimbine obtained was dried. The filtrate was extracted with a half volume of methylene chloride at pH 1.5. The extraction was repeated twice, using a half volume of methylene chloride each time. Finally the methylene chloride was evaporated to give 2.3 g of D(+)-alpha-(N-pyrrolyl)-phenylacetic acid, rotatory power +83°.

The first insoluble solid was resuspended in 1 liter of water at 40°-45° C., was adjusted to pH 9 with 2N ammonium hydroxide, the pH being maintained for half an hour. It was cooled to 4° C. for one hour and filtered. The filtrate was extracted twice with methylene chloride at pH 1.5, using ½ volume each time. Finally the methylene chloride was evaporated off to give 6 g of L(−)-alpha-(N-pyrrolyl)-phenylacetic acid, rotatory power −20°.

The 26 g of yohimbine alpha-(N-pyrrolyl)-phenylacetate were resuspended in a mixture of 1460 ml of water and 137 ml of ethanol. The mixture was heated to boiling for one hour and thereafter was filtered while warm. The dry insoluble product weighed 5 g. The filtrate was allowed to crystallise at room temperature first and was then left in a refrigerator overnight. It was then filtered and washed with water, followed by drying at 40° C. under vacuum. The dry product weighed 16 g. The mother liquors were concentrated under vacuum to the onset of crystallisation and the pH was adjusted to 9 with 2N NaOH. The liquors were allowed to crystallise cold for one hour, were filtered and washed with water. The filtrate was extracted twice with methylene chloride at pH 1.5, using ½ volume each time. Finally the organic phases were reunited and D(+)-alpha-(N-pyrrolyl)-phenylacetic acid was precipitated out. After drying, it weighed 1.3 g with a rotatory power of +49.6°. The insoluble product obtained in this second recrystallisation was treated in the same way as indicated above to give 1.6 g of L(−)-alpha-(N-pyrrolyl)-phenylacetic acid, with a rotatory power of −17°.

The 16 g of yohimbine alpha-(N-pyrrolyl)-phenylacetate were recrystallised following the same technique as indicated above, to give 3.2 g of insoluble salt which was converted into L(−)-alpha-(N-pyrrolyl)-phenylacetic acid weighing 1 g with a rotatory power of −17.5°.

The recrystallised yohimbine salt weighed 9.3 g and after conversion into acid, 3 g of L(−)-alpha-(N-pyrrolyl)-phenylacetic acid with a rotatory power of −19.2° were obtained.

EXAMPLE 8

Figure 3:
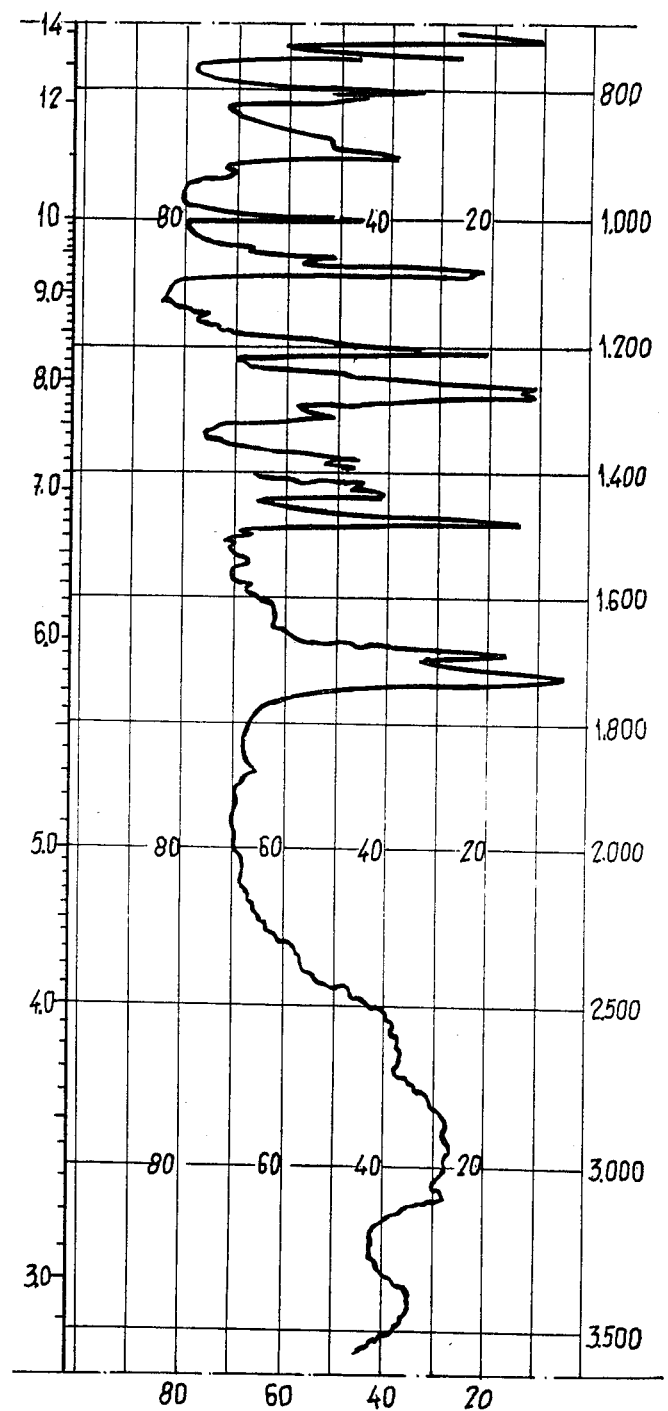
FIG. 3 is the same for alpha-(N-pyrrolyl)-p-chlorophenyl-propionic acid.

Alpha-(N-pyrrolyl)-p-chlorophenyl propionic acid 48 g of sodium acetate were dissolved in 480 cc of acetic acid. The solution was heated to boiling and then 24 g (0.091 mole) of p-chlorophenylaniline ethyl ester hydrochloride followed by 13.5 g (0.097 mole) of 2,5-dimethoxytetrahydrofuran were added. After allowing to react at room temperature for one minute, the reaction mixture was poured over 950 g of ice water. The mixture was extracted with 900 ml of ethyl acetate. The alpha-(N-pyrrolyl)-derivative ester was obtained by evaporation of the ethyl acetate. Thereafter the product was hydrolysed with an alkali in dioxane-water in a way similar to that described in the previous Examples. After removal of the dioxane, the mixture was extracted at pH 1.5-2 with chloroform, from which the product was crystallised with petroleum ether. After drying the alpha-(N-pyrrolyl)-p-chlorophenyl propionic acid obtained weighed 15.2 g with m.p. 124°-126° C. The IR spectrum in 0.5% KBr is given in FIG. 3.

Hereinafter there are given the results of tests conducted on the therapeutic properties of the compounds according to the invention.

Platelet anti-aggregation activity

It has been known for many years that platelet aggregation plays a fundamental role in hemostasis and in thrombotic pathogenesis, mainly arterial.

Platelet aggregation is usually studied "in vitro" by a photometric technique (aggregometer) described by G. V. R. Born, Nature, 194, 927 (1962).

Wistar rats, ITA 177 SPF, body weight 100–250 g, were used for studying ADP induced platelet aggregation "ex vivo" in rats.

Acetylsalicyclic acid at a dose level of 100 mg/kg p.o. was used as standard.

The products to be tested were administered at the maximum dose of 200 mg/kg, p.o.

Both the standard and the products were administered dissolved or suspended in a 10 ml/kg Tween solution.

The animals were fasted during the test and for 17 hours prior thereto, but had water "ad libitum".

5 hours after administration of the products, the animals (5 per group) were anaesthetised and blood was drawn from the jugular vein using a syringe containing 3.8% sodium citrate.

The % aggregation was calculated measuring the difference in mm in the recorder between the initial aggregation stage and the height of the specimen curve 6 minutes after the onset of aggregation.

This figure, therefore, is calculated as a percentage, taking as 100% the figure in mm of the difference between the platelet rich plasma (prp) and the platelet poor plasma (ppp) obtained in balancing the apparatus for the specimen under examination.

The results obtained are given in Table I below:

The material used consisted of lots of NMRI mice bred in our SPF breeding centre under constant temperature and humidity conditions of 23°±0.5° C. and 70±5%.

Standard: acetylsalicylic acid
Vehicle: propylene glycol/water—40/60 v.
Transparent plastic cages.

With this material the mice were randomly distributed into groups of 10 animals. The test order and the treatment to be given to each group was also randomised.

The mice were fasted for 15–18 hours, with water "ad libitum" and the allotted treatments were administered p.o., (10 mg/kg), dissolved or suspended in the vehicle.

The control lot received the vehicle. As standard, acetylsalicylic acid at a dose level of 100 mg/kg, suspended in the same vehicle and administered p.o., was used.

After 30 minutes, 0.25 ml per 20 g body weight of a

TABLE I

| | "Ex vivo" platelet anti-aggregation activity in rats | | | | |
|---|---|---|---|---|---|
| | Dose | No | mean | Platelet aggregation | |
| Treatment | mg/kg p.o. | animals | weight in g. | % | % inhibition |
| Control | — | 5 | 160.0 ± 4.47 | 86.4 ± 2.15 | — |
| Acetylsalicylic acid | 100 | 5 | 160.0 ± 3.16 | 20.1 ± 1.49 | 76.7 |
| Phenylbutazone | 100 | 5 | 160.0 ± 5.48 | 58.2 ± 7.35 | 32.6 |
| DL(±)-alpha-(N—pyrrolyl)-phenylacetic acid | 100 | 5 | 158.0 ± 3.74 | 25.3 ± 9.28 | 70.7 |
| Alpha-(N—pyrrolyl)-acetic acid | 100 | 5 | 158.0 ± 3.74 | 63.1 ± 3.32 | 27.0 |
| Ethyl DL(±)-alpha-(N—pyrrolyl)-phenylacetate | 100 | 5 | 162.0 ± 3.74 | 42.0 ± 2.58 | 51.4 |

Duncan Kramer test, p < 0.05

Peripheral analgesic activity—acetic acid contractions

Drugs having a predominantly pain-suppressing action are known as analgesics and are classed usually as narcotics and non-narcotics.

The non-narcotics do not induce sleepiness nor provoke addiction and are inoperative against certain pain pictures. The most characteristic among this group are the salicylates.

The experimental method consists of injecting an irritant, such as acetic acid, into the rat peritoneum and provoking obviously appreciable painful contorsions such as stretching of the rear paws and twisting of the dorso-abdominal muscles.

The action mechanism of acetylsalicylic acid as an analgesic appears to operate at two levels, one central and the other peripheral, antagonisin the action of bradykinin peripherally, either where the nociceptive stimulus occurs or by preventing the passage of the latter at the blood-brain barrier.

0.5% acetic acid solution was administered intraperitoneally.

15 minutes were allowed to elapse, after which the mice were observed for half an hour, placing each one in an upturned transparent plastic cage.

The number of painful contorsions were counted and, for evaluating the results, the means of the number of stretches of each lot were calculated and were expressed as inhibition percentages relative to the control, as per the following equation:

$$\% \text{ protection} = \frac{c - b}{c} \times 100$$

where c is the mean of the number of stretches of the control group and b is the mean of the number of stretches of the treated group.

The statistical significance between the lots may be ascertained with the Duncan-Kramer test, with $p < 0.05$.

The results obtained are given in Table II below:

TABLE II

| | Analgesic activity | | | |
|---|---|---|---|---|
| | 0.5% acetic acid induced contorsions in NMRI mice male (n = 10) | | | |
| Treatment | Dose mg/kg | No contorsions $\bar{X} \pm$ s.e. | % inhibition relative to control | No mice with contorsions |
| Control | 100 | 27.1 ± 4.3 | — | 10/10 |
| Acetylsalicylic acid | 100 | 17 ± 3.5 | 37.27 | 10/10 |
| DL(±)-alpha-(N—pyrrolyl)-phenylacetic acid | 100 | 5.5 ± 1.8 | 79.7 | 7/10 |
| D(+)-alpha-(N— | 100 | 7.9 ± 2.6 | 70.9 | 8/10 |

TABLE II-continued

| Treatment | Analgesic activity 0.5% acetic acid induced contorsions in NMRI mice male (n = 10) | | | |
|---|---|---|---|---|
| | Dose mg/kg | No contorsions $\overline{X} \pm$ s.e. | % inhibition relative to control | No mice with contorsions |
| pyrrolyl)-phenylacetic acid | | | | |
| L(−)-alpha-(N—pyrrolyl)-phenylacetic acid | 100 | 6.4 ± 1.9 | 76.2 | 8/10 |
| Dibenzylammonium DL(±)-alpha-(N—pyrrolyl)-p-hydroxyphenylacetate | 100 | 7.5 ± 2.2 | 72.3 | 9/10 |

Duncan Kramer test: $p < 0.05$

What we claim is:

1. Dibenzylammonium DL(±)-alpha-(N-pyrrolyl)-p-hydroxy-phenylacetate.

2. Pharmaceutical composition having analgesic and platelet anti-aggregation activity comprising an analgesic or platelet anti-aggregation therapeutically effective amount of at least one compound selected from the group consisting of
   ethyl DL(±)-alpha-(N-pyrrolyl)-phenylacetate,
   dibenzylammonium DL(±)-alpha-(N-pyrrolyl)-p-hydroxy-phenylacetate,
   DL(±)-alpha-(N-pyrrolyl)-phenylacetic acid,
   D(+)-alpha-(N-pyrrolyl)-phenylacetic acid, and
   L(−)-alpha-(N-pyrrolyl)-phenylacetic acid,
in association with at least one of (a) an excipient, and (b) a pharmaceutically acceptable dissolution or suspension vehicle.

3. Composition of claim 2 wherein said compound is ethyl DL(±)-alpha-(N-pyrrolyl)-phenylacetate.

4. Composition of claim 2 wherein said compound is dibenzylammonium DL(±)-alpha-(N-pyrrolyl)-p-hydroxy-phenylacetate.

5. Composition of claim 2 wherein said compound is DL(±)-alpha-(N-pyrrolyl)-phenylacetic acid.

6. Composition of claim 2 wherein said compound is D(+)-alpha-(N-pyrrolyl)-phenylacetic acid.

7. Composition of claim 2 wherein said compound is L(−)-alpha-(N-pyrrolyl)-phenylacetic acid.

8. Method for analgesic pain-suppressing treatment of a host capable of experiencing pain comprising administering to said host an analgesic effective amount of the composition of the claim 2.

9. Method of claim 8 wherein the compound of said composition is ethyl DL(±)-alpha-(N-pyrrolyl)-phenylacetate.

10. Method of claim 8 wherein the compound of said composition is dibenzylammonium DL(±)-alpha-(N-pyrrolyl)-p-hydroxy-phenylacetate.

11. Method of claim 8 wherein the compound of said composition is DL(±)-alpha-(N-pyrrolyl)-phenylacetic acid.

12. Method of claim 8 wherein the compound of said composition is D(+)-alpha-(N-pyrrolyl)-phenylacetic acid.

13. Method of claim 8 wherein the compound of said composition is L(−)-alpha-(N-pyrrolyl)-phenylacetic acid.

* * * * *